US012693820B2

(12) United States Patent (10) Patent No.: US 12,693,820 B2
Takemura et al. (45) Date of Patent: Jul. 28, 2026

(54) DISPLAY APPARATUS, MEDICAL INFORMATION DISPLAY SYSTEM, RECORDING MEDIUM, AND DISPLAY METHOD

(71) Applicant: Konica Minolta, Inc., Tokyo (JP)

(72) Inventors: Tomoaki Takemura, Hachioji (JP); Hidekazu Takahashi, Toyonaka (JP); Hisashi Wada, Nerima-ku (JP); Kei Okabayashi, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 498 days.

(21) Appl. No.: 18/318,324

(22) Filed: May 16, 2023

(65) Prior Publication Data

US 2023/0377725 A1 Nov. 23, 2023

(30) Foreign Application Priority Data

May 17, 2022 (JP) ................................. 2022-080578

(51) Int. Cl.
*G16H 30/40* (2018.01)
*G06F 3/14* (2006.01)
(Continued)

(52) U.S. Cl.
CPC .............. *G16H 30/40* (2018.01); *G06F 3/14* (2013.01); *G06T 7/0012* (2013.01); *G06V 10/56* (2022.01);
(Continued)

(58) Field of Classification Search
CPC ........ G16H 30/40; G16H 30/20; G06V 10/56; G06V 10/60; G06F 3/14; G06T 7/0012; G06T 2207/30096
(Continued)

(56) References Cited

U.S. PATENT DOCUMENTS 7,616,793 B2 * 11/2009 Marshall ................ G16H 50/20
382/128
11,164,314 B2 * 11/2021 Smith ....................... G06T 7/30
(Continued)

FOREIGN PATENT DOCUMENTS

JP H0935043 A 2/1997
JP 2006115921 A 5/2006
(Continued)

OTHER PUBLICATIONS

JPO Notice of Reasons for Refusal for corresponding JP Application No. 2022-080578; Issued Nov. 19, 2024.

*Primary Examiner* — Gabriel I Garcia
(74) *Attorney, Agent, or Firm* — CANTOR COLBURN LLP

(57) ABSTRACT

A display apparatus includes: a hardware processor configured to cause a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the hardware processor distinguishably displays the first display information and the second display information.

17 Claims, 7 Drawing Sheets

(51) Int. Cl.

| | | |
|---|---|---|
| *G06T 7/00* | (2017.01) | |
| *G06V 10/56* | (2022.01) | |
| *G06V 10/60* | (2022.01) | |
| *G16H 30/20* | (2018.01) | |

(52) U.S. Cl.
CPC ............ *G06V 10/60* (2022.01); *G16H 30/20* (2018.01); *G06T 2207/30096* (2013.01)

(58) Field of Classification Search
USPC ........................................................ 382/128
See application file for complete search history.

(56) References Cited

U.S. PATENT DOCUMENTS

| 11,580,643 B2 * | 2/2023 | Huang | .................. G06T 11/203 |
|---|---|---|---|
| 2019/0266722 A1 * | 8/2019 | Sugahara | ............... G16H 30/40 |
| 2022/0061746 A1 * | 3/2022 | Lyman | .................. G16H 30/20 |

FOREIGN PATENT DOCUMENTS

| JP | 20060115921 A | 5/2006 | |
|---|---|---|---|
| JP | 2011110173 A | 6/2011 | |
| WO | 2011132468 A1 | 10/2011 | |
| WO | WO-2022029824 A1 * | 2/2022 | ........... A61B 1/0005 |

* cited by examiner

FIG.1

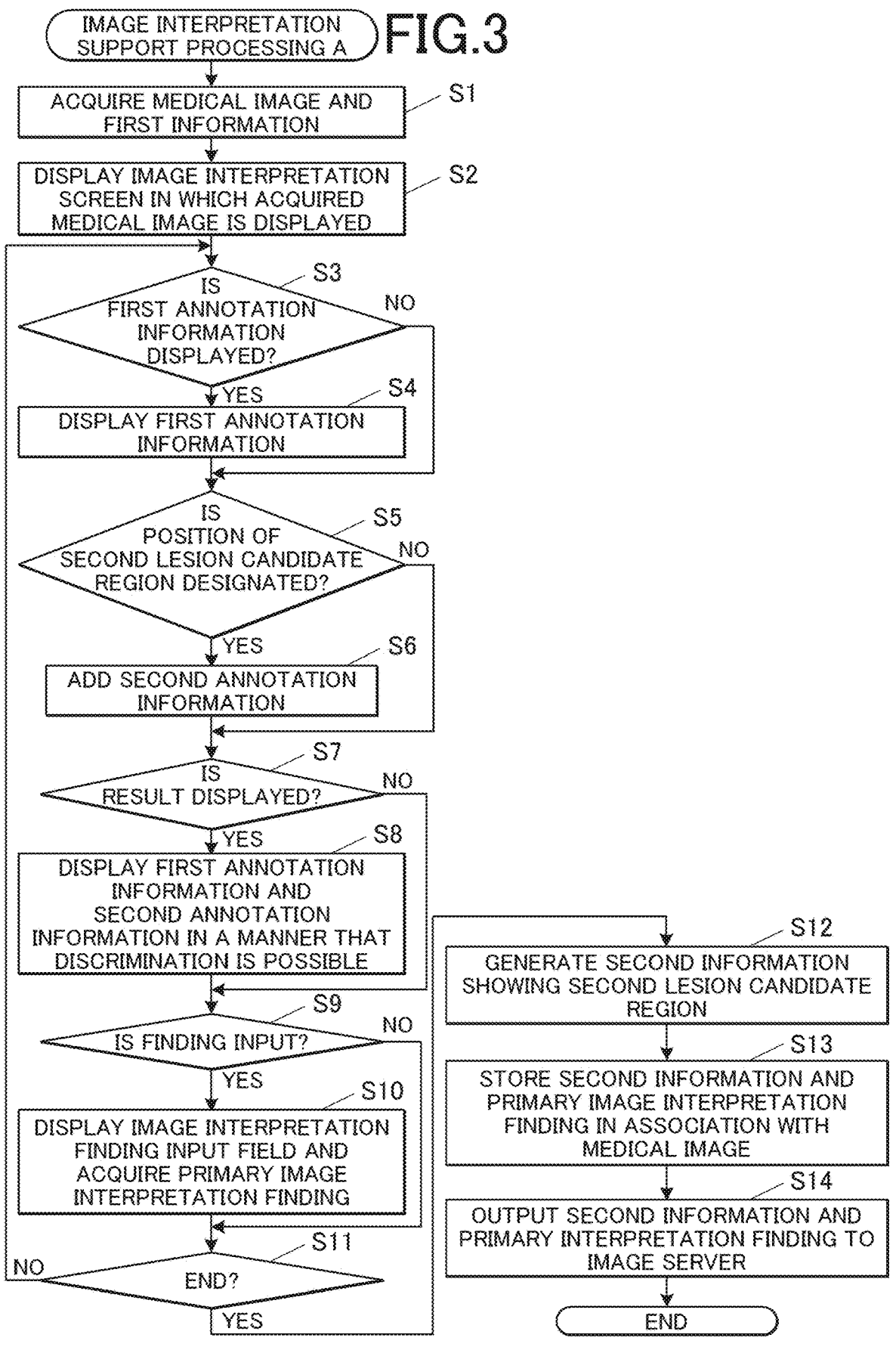

FIG.3

IMAGE INTERPRETATION SUPPORT PROCESSING A

ACQUIRE MEDICAL IMAGE AND FIRST INFORMATION — S1

DISPLAY IMAGE INTERPRETATION SCREEN IN WHICH ACQUIRED MEDICAL IMAGE IS DISPLAYED — S2

S3 IS FIRST ANNOTATION INFORMATION DISPLAYED? — NO / YES

DISPLAY FIRST ANNOTATION INFORMATION — S4

S5 IS POSITION OF SECOND LESION CANDIDATE REGION DESIGNATED? — NO / YES

ADD SECOND ANNOTATION INFORMATION — S6

S7 IS RESULT DISPLAYED? — NO / YES

DISPLAY FIRST ANNOTATION INFORMATION AND SECOND ANNOTATION INFORMATION IN A MANNER THAT DISCRIMINATION IS POSSIBLE — S8

S9 IS FINDING INPUT? — NO / YES

DISPLAY IMAGE INTERPRETATION FINDING INPUT FIELD AND ACQUIRE PRIMARY IMAGE INTERPRETATION FINDING — S10

S11 END? — NO / YES

GENERATE SECOND INFORMATION SHOWING SECOND LESION CANDIDATE REGION — S12

STORE SECOND INFORMATION AND PRIMARY IMAGE INTERPRETATION FINDING IN ASSOCIATION WITH MEDICAL IMAGE — S13

OUTPUT SECOND INFORMATION AND PRIMARY INTERPRETATION FINDING TO IMAGE SERVER — S14

END 461a     461

○×TARO PATIENT ID:001 AGE45 EXAMINATION DATE 2022/2/2

461b

| MARK DISPLAY | RESULT DISPLAY | FINDING INPUT | END |
|---|---|---|---|

461h     461g     461c     461d     461e 461a     461

○×TARO PATIENT ID:001 AGE45 EXAMINATION DATE 2022/2/2

IMAGE
MEASURE
PULMONARY NODULE MARK
LUT

CIRCLE
QUADRANGLE
ARROW
FREE CURVE

CANNOT BE SELECTED BECAUSE SAME AS ANALYSIS RESULT MARK 51
53
54
52

| MARK DISPLAY | RESULT DISPLAY | FINDING INPUT | END |
|---|---|---|---|

○×TARO  PATIENT ID:001  AGE45  EXAMINATION DATE 2022/2/2

461b

51

53

52

| IMAGE | ▶ |
| MEASURE | ▶ |
| PULMONARY NODULE MARK | ▶ | CIRCLE |
| LUT | ▶ | QUADRANGLE |
| | | ARROW |
| | | FREE CURVE |

461h    ◁ ▷ 461g    MARK DISPLAY    RESULT DISPLAY    FINDING INPUT    END 461c  461d    461e

○×TARO  PATIENT ID:001  AGE45  EXAMINATION DATE 2022/2/2

55

461b

MESSAGE  ✕

CANNOT BE DISPLAYED
BECAUSE SAME AS ANALYSIS
RESULT MARK

461h    ◁ ▷ 461g    MARK DISPLAY    RESULT DISPLAY    FINDING INPUT    END 461c  461d    461e

○×TARO  PATIENT ID:001  AGE45  EXAMINATION DATE 2022/2/2

55

461b

MESSAGE  ✕

CANNOT BE DISPLAYED
BECAUSE SAME AS ANALYSIS
RESULT MARK
PERMIT CHANGE TO MARK
THAT CAN BE DISPLAYED?

56    PERMIT    CANCEL

461h    ◁ ▷ 461g    MARK DISPLAY    RESULT DISPLAY    FINDING INPUT    END 461c  461d    461e 461a　　461　461b　A1　A2

MARK DISPLAY　RESULT DISPLAY　FINDING INPUT　END 461h　461g　461c　461d　461e 461a　461　461f

FINDING

PLURALITY OF NODULAR SHADOW IN LEFT UPPER LOBE

461b

MARK DISPLAY　RESULT DISPLAY　FINDING INPUT　END 461h　461g　461c　461d　461e

DISPLAY APPARATUS, MEDICAL INFORMATION DISPLAY SYSTEM, RECORDING MEDIUM, AND DISPLAY METHOD

CROSS REFERENCE TO RELATED APPLICATIONS

The present invention claims priority under 35 U.S.C. § 119 to Japanese Application, 2022-080578, filed on May 17, 2022, the entire contents of which being incorporated herein by reference.

TECHNICAL FIELD

The present invention relates to a display apparatus, a medical information display system, a recording medium, and a display method.

DESCRIPTION OF THE RELATED ART

Generally, a picture archiving and communication system (PACS) viewer has a function of adding annotations such as a circle (ellipse), a quadrangle, a polygon, and the like to a lesion in a medical image by operation by a user such as a doctor.

Recently, systems have been disclosed which can automatically detect a lesion candidate region in an image by performing, on a medical image such as a CT image, a CR image, or an MRI image, computer processing such as artificial intelligence (AI) analysis based on machine learning or deep learning technology.

For example, Japanese Patent No. 4651353 discloses that a portion checked by a doctor in image interpretation and a portion detected by analysis processing using a diagnostic support system (computer aided diagnosis (CAD)) are annotated and displayed.

Japanese Unexamined Patent Publication No. 2011-110173 discloses that "(A) an annotation provided by CAD" and "(B) an annotation provided by a user" are printed and output on a film in a distinguished manner by adding identification information (a character, a writing, a figure, or the like) to "(A) an annotation provided by CAD".

SUMMARY OF THE INVENTION

Japanese Patent No. 4651353 describes that an analysis result of a diagnostic support system is displayed so as to be superimposed on a diagnostic result (check result) by a doctor and that the doctor re-interprets a difference between both. In Japanese Patent No. 4651353, when an analysis result of a diagnostic support system and a diagnostic result of a doctor are superimposed and displayed, a portion extracted by CAD and a portion checked by the doctor are displayed differently by coincidence (FIG. 4). However, in Japanese Patent No. 4651353, the color of the annotation of the portion checked by the doctor is changed according to the number of times of the interpretation (paragraph [0017]). Therefore, depending on the number of times of interpretation, there is a possibility that a portion extracted by the CAD and a portion checked by the doctor have the same annotation. As a result, the two may not be distinguished from each other.

Actually, in Japanese Patent No. 4651353, the annotation attached to the portion extracted only by the CAD which was not checked by the doctor (FIG. 7), and the annotation attached to the portion which was checked only by the doctor but overlooked by the CAD (FIG. 8)) are the same annotation. As a result, a situation arises in which it is not possible to distinguish which one added the annotation.

In addition, according to an operation rule on the hospital side, it is not possible to distinguish between an annotation by detection of an AI including a CAD in the related art and an annotation indicating a check place of a doctor, and thus a situation in which the interpretation work is hindered may occur.

For example, as a rule of the diagnostic support system, there is a case where an operation is performed in which, for example, a circular annotation is provided to a pulmonary nodule detected by AI in, for example, a grayscale softcopy presentation state (GSPS) format.

The annotation can be set when the GSPS is created.

However, once determined, a circular annotation is fixedly given to the pulmonary nodule. On the other hand, independently thereof, as a rule in the hospital at the time of the interpretation, there is a case where in practice, a user such as a radiologist adds a circular annotation to the pulmonary nodule. In such a case, the annotation on the pulmonary nodule by the user (radiologist) and the annotation by the detection of the AI have the same shape, and there is a possibility that the annotation by the detection of the radiologist and the annotation by the detection of the AI cannot be distinguished from each other.

Even if the rule at the time of interpretation is determined in advance on the hospital side in accordance with the setting of the diagnostic support system, it takes time and effort for the doctor to perform the operation of adding the annotation, which may hinder the quick interpretation operation.

For example, in a case where the practice is such that the annotation attached by AI detection is changed depending on the disease type (e.g., nodule type), the doctor has to grasp all annotations attached as the detection result of AI in advance and attach different annotations depending on the disease type. Therefore, the work of the doctor becomes very complicated.

In this point, Japanese Unexamined Patent Publication No. 2011-110173 discloses that, as described above, by adding identification information (a character, a writing, a figure, or the like) to "(A) an annotation provided by CAD", "(A) an annotation provided by CAD" and "(B) an annotation provided by a user" are output distinctively. However, in Japanese Unexamined Patent Publication No. 2011-110173, the problem is the distinguishability of (A) and (B) when externally outputted. That is, it is merely described in Japanese Unexamined Patent Publication No. 2011-110173 that (A) and (B) are distinguished and output when externally output. When externally output is when printing is performed on a film.

In the case of displaying on the display part (viewer) in Japanese Unexamined Patent Publication No. 2011-110173, it is possible to select whether or not (A) and (B) are individually displayed. Therefore, Japanese Unexamined Patent Publication No. 2011-110173 states that the difference between (A) and (B) can be easily determined (paragraph [0007]). That is, in Japanese Unexamined Patent Publication No. 2011-110173, (A) and (B) can be identified on the display part (viewer), and the distinguishability at the time of interpretation by displaying on the display is not the problem.

However, while the annotation by the user (e.g., the primary radiologist) high reliability, annotations by AI detection may include many false positives. Therefore, in a case where the next radiologist makes a diagnosis in a state where it is not possible to distinguish between the annotation according to the radiologist and the annotation according to detection by the AI, the image interpretation has to be performed in a state where a highly reliable annotation added by a user and a not so reliable annotation added by detection by the AI are mixed. As a result, there is a possibility that a lesion that should be viewed is overlooked.

In addition, the AI detection result cannot be used as the final definitive diagnosis. Therefore, the radiologist needs to check the AI detection result. However, in a state in which it is not possible to distinguish which of the radiologist and the AI performed the detection for the annotation, there is a possibility that the final radiologist overlooks the AI detection result that should be actually viewed and makes a final diagnosis without confirming the result.

The present invention has been made in consideration of the above-described problems in the related art, and an object of the present invention is to prevent a doctor from overlooking a lesion that should be viewed when the doctor interprets a medical image by displaying a detection result of a lesion candidate region obtained by computer processing on medical information and a detection result of a lesion candidate region obtained by a user.

To achieve at least one of the abovementioned objects, according to an aspect of the present invention, a display apparatus reflecting one aspect of the present invention includes, a hardware processor configured to cause a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the hardware processor distinguishably displays the first display information and the second display information.

To achieve at least one of the abovementioned objects, according to an aspect of the present invention, a display apparatus reflecting one aspect of the present invention includes, a hardware processor configured to, acquire first information indicating a first lesion candidate region obtained by computer processing on medical information, acquire second information indicating a second lesion candidate region specified by a first user based on the medical information, cause a display part to simultaneously display first display information based on the first information and second display information based on the second information, and acquire an image interpretation finding created by a second user based on the medical information, wherein, in a case where the first display information and the second display information are displayed at the same time, the hardware processor distinguishably displays the first display information and the second display information, and wherein the hardware processor acquires the image interpretation finding based on a confirmation result of the first display information and the second display information by the second user.

To achieve at least one of the abovementioned objects, according to an aspect of the present invention, a medical information display system reflecting one aspect of the present invention includes, a hardware processor configured to cause a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the hardware processor distinguishably displays the first display information and the second display information.

To achieve at least one of the abovementioned objects, according to an aspect of the present invention, a medical information display system reflecting one aspect of the present invention includes, a hardware processor configured to, acquire first information indicating a first lesion candidate region obtained by computer processing on medical information, acquire second information indicating a second lesion candidate region specified by a first user based on the medical information, cause a display part to simultaneously display first display information based on the first information and second display information based on the second information, and acquire an image interpretation finding created by a second user based on the medical information, wherein, in a case where the first display information and the second display information are displayed at the same time, the hardware processor distinguishably displays the first display information and the second display information, and acquires the image interpretation finding based on a confirmation result of the first display information and the second display information by the second user.

To achieve at least one of the abovementioned objects, according to an aspect of the present invention, a recording medium reflecting one aspect of the present invention includes, a computer-readable program causing a computer to perform, causing a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the first display information and the second display information are distinguishably displayed.

To achieve at least one of the abovementioned objects, according to an aspect of the present invention, a recording medium reflecting one aspect of the present invention includes a computer-readable program causing a computer to perform, first acquiring to acquire first information indicating a first lesion candidate region obtained by computer processing on medical information, second acquiring to acquire second information indicating a second lesion candidate region specified by a first user based on the medical information, displaying to cause a display part to simultaneously display first display information based on the first information and second display information based on the second information, and third acquiring to acquire an image interpretation finding created by a second user based on the medical information, wherein in a case where the first display information and the second display information are displayed at the same time, in the displaying, the first display information and the second display information are distinguishably displayed, and wherein in the third acquiring, the image interpretation finding is acquired based on a confirmation result of the first display information and the second display information by the second user.

To achieve at least one of the abovementioned objects, according to an aspect of the present invention a display method reflecting one aspect of the present invention includes, causing a display part to simultaneously display first display information indicating a first lesion candidate region obtained by computer processing on medical information and second display information indicating a second lesion candidate region specified by a user on the basis of the medical information, and in a case where the first display information and the second display information are displayed at the same time, distinguishably displaying the first display information and the second display information.

To achieve at least one of the abovementioned objects, according to an aspect of the present invention, a display method reflecting one aspect of the present invention includes, first acquiring to acquire first information indicating a first lesion candidate region obtained by computer processing on medical information, second acquiring to acquire second information indicating a second lesion candidate region specified by a first user based on the medical information, displaying to cause a display part to simultaneously display first display information based on the first information and second display information based on the second information, and third acquiring to acquire an image interpretation finding created by a second user based on the medical information, wherein, in a case where the first display information and the second display information are displayed at the same time, in the displaying, the first display information and the second display information are distinguishably displayed, and in the third acquiring, the image interpretation finding is acquired based on a confirmation result of the first display information and the second display information by the second user.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 1 is an overall configuration diagram of a medical information display system according to the present embodiment.

FIG. 3 is a flowchart showing the flow of image interpretation support processing A executed by the controller in FIG. 2.

FIG. 6A is a diagram showing an example in which first display candidate information and second display candidate information are selectably displayed on the image interpretation screen.

FIG. 6B is a diagram illustrating an example of a notification screen displayed when the second display candidate information is selected in FIG. 6A.

FIG. 6C is a diagram showing another example of the notification screen displayed when the second display candidate information is selected in FIG. 6A.

DETAILED DESCRIPTION

Figure 2:
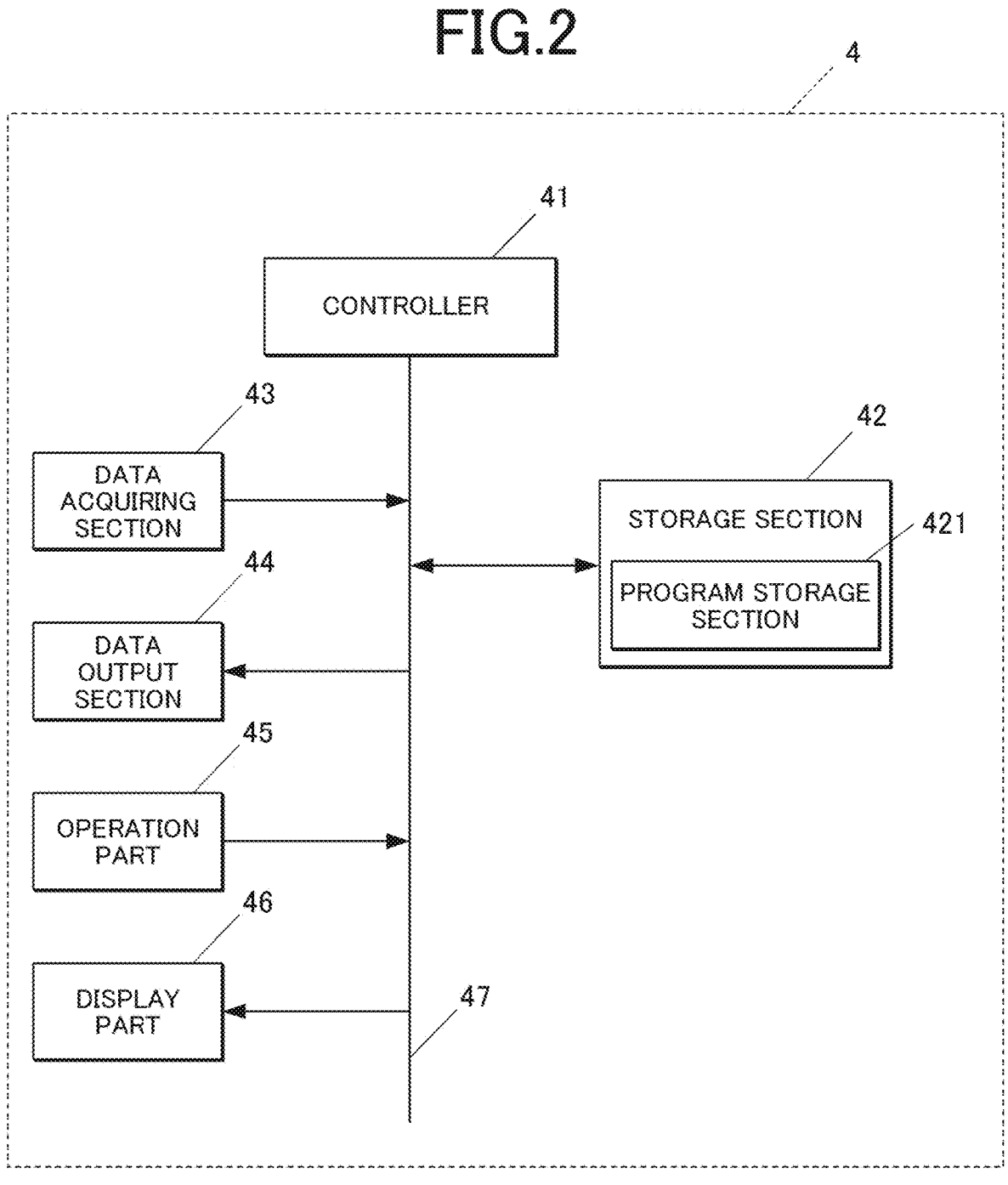
FIG. 2 is a main part block diagram showing a functional configuration of an image interpretation terminal in FIG. 1.

Hereinafter, preferred embodiments according to the present invention will be described with reference to the drawings. However, the scope of the invention is not limited to the disclosed embodiments.

First Embodiment

[Configuration of Medical Information Display System]

Figure 1:
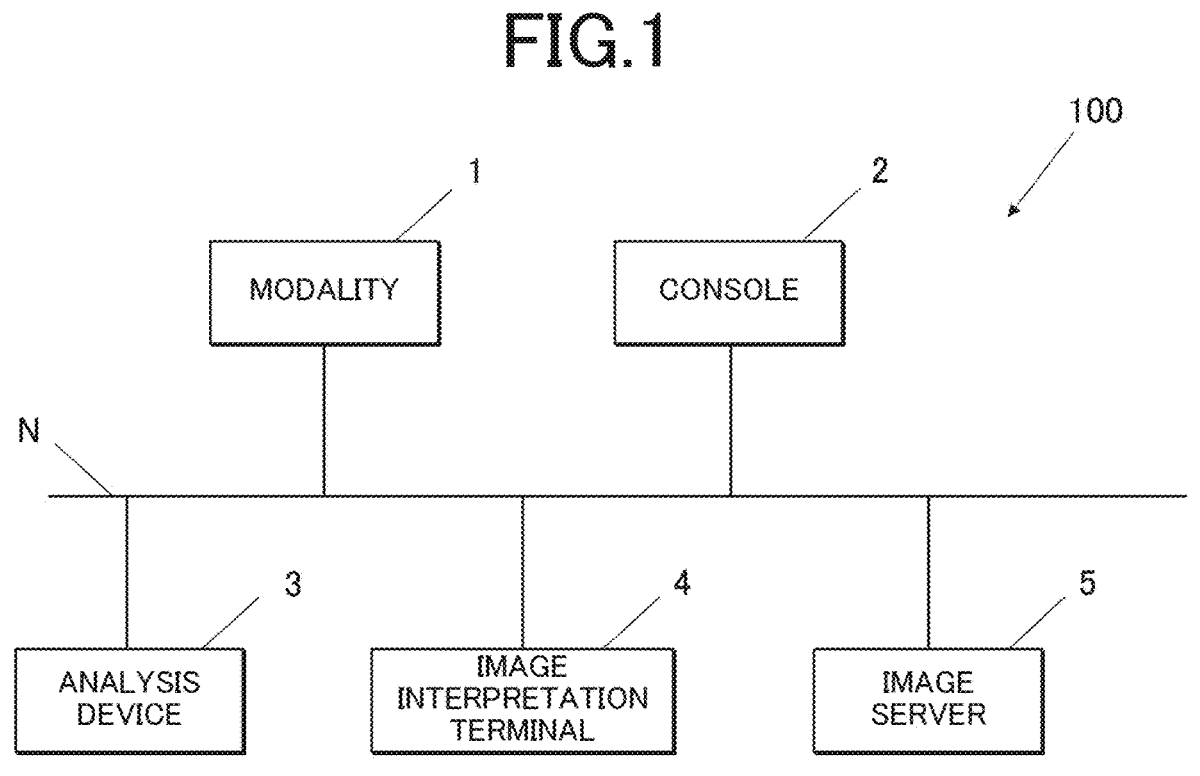

FIG. 1 illustrates a system configuration example of a medical information display system 100 according to the first embodiment.

As illustrated in FIG. 1, the medical information display system 100 includes a modality 1, a console 2, an analysis device 3, an image interpretation terminal 4, an image server 5, and the like. Each apparatus constituting the medical information display system 100 is connected via a communication network N such as a local area network (LAN), a wide area network (WAN), or the Internet. Each apparatus constituting the medical information display system 100 is compliant with the HL7 (Health Level Seven) or DICOM (Digital Image and Communications in Medicine) standard. Communication between the apparatuses is performed in accordance with HL7 or DICOM. The number of modalities 1, the console 2, the analysis device 3, the image interpretation terminal 4, and the like is not particularly limited.

The modality 1 is an image generation apparatus such as an X-ray imaging apparatus (DR, CR), an ultrasound diagnostic apparatus (US), CT, or MRI, for example. The modality 1 images an examination target site of a patient as a subject and generates a medical image as medical information based on examination order information transmitted from a radiology information system (RIS) or the like (not illustrated). In the medical image generated in the modality 1, supplementary information is written, for example, in a header of an image file in accordance with the DICOM standard. The supplementary information includes patient information, examination information, and identification information of a medical image. The patient information includes a patient ID, patient name, date of birth, age, sex, height, weight, and the like. The examination information includes an examination ID, an examination date and time, a type of modality, an examination site, a requested department, and an examination purpose. The identification information of the medical image is, for example, a unique ID (UID). The medical image to which the supplementary information is thus attached is transmitted to the analysis device 3 or the image server 5 via the console 2 or the like.

The console 2 is an imaging control device that controls imaging in the modality 1. The console 2 outputs the imaging conditions and the image reading conditions to the modality 1 and acquires image data of the medical image captured in the modality 1. The console 2 is configured to comprise a controller, a display part, an operation part, a communication unit, a storage section, and the like (not shown), and each unit is connected by a bus.

The analysis device 3 is a device that analyzes a medical image that is medical information. The analysis device 3 is configured as a personal computer (PC), a mobile terminal, or a dedicated device. The analysis device 3 is configured to include a controller, a display part, an operation part, a communication unit, a storage section, and the like, which are not illustrated. The units of the analysis device 3 are connected to each other via a bus.

For example, the analysis device 3 analyzes the medical image which is the medical information transmitted from the console 2 by computer processing to detect a lesion candidate region. Here, as the computer processing, for example, AI analysis using AI, including detection of a lesion candidate region by CAD, is used. The analysis device 3 adds identification information of the medical image of a detection source to information (information regarding the first lesion candidate region) indicating the lesion candidate region (first lesion candidate region) obtained by computer processing and transmits the information to the image server 5 through the communication unit. Information about the first lesion candidate region is referred to as first information. There may be one or a plurality of first lesion candidate regions in one medical image. In some cases, it does not exist.

The first information is generated for each medical image of the detection source. In the present embodiment, a file in a GSPS format is used as the first information. The first information includes, for example, the kind of lesion, position information, and display information indicating the first lesion candidate region on the medical image for each of the first lesion candidate regions. Display information indicating the first lesion candidate region on the medical image is referred to as first display information. The position information shows coordinates or the like on the medical image. Examples of kinds of lesions include, but not limited to, nodule and mass. The kind of lesion may be, for example, a lesion that is classified in more detail, such as a nodule type (solid, P-solid, GGN, or the like). The first display information is, for example, an annotation. The first display information is different for each kind (or type) of lesion. The annotation as the first display information, that is, the annotation indicating the first lesion candidate region is referred to as first annotation information.

In the present embodiment, a case where the first display information is the first annotation information will be described as an example.

The image interpretation terminal 4 is, for example, a client (PACS viewer) of a picture archiving and communication system (PACS). The image interpretation terminal 4 is a display apparatus that reads a medical image which is medical information or first information from the image server 5 or the like and displays the medical image or the first information for interpretation.

The user (radiologist) interprets the medical image on the image interpretation terminal 4 and creates an image interpretation finding (image interpretation report or the like) of the radiologist regarding the medical image.

FIG. 2 is a block diagram illustrating the functional configuration of an image interpretation terminal 4.

As shown in FIG. 2, the image interpretation terminal 4 includes a controller 41 (hardware processor), a storage section 42, a data acquiring section 43, a data output section 44, an operation part 45, a display part 46, and the like. The respective units of the image interpretation terminal 4 are connected by a bus 47.

The controller 41 includes a central processing unit (CPU), a random access memory (RAM), and the like. The controller 41 comprehensively controls the operation of each section of the image interpretation terminal 4. Specifically, the CPU of the controller 41 reads various processing programs stored in a program storage section 421 of the storage section 42, deploys the programs to a RAM, and executes various types of processing in accordance with the programs.

The storage section 42 is configured by a hard disk drive (HDD), a semiconductor memory, or the like. The storage section 42 includes a program storage section 421 that stores programs for executing various processes including an image interpretation support processing A and an image interpretation support processing B to be described later. The storage section 42 stores parameters, files, and the like required for execution of the program stored in the program storage section 421.

The data acquiring section 43 is composed of, for example, a network interface. The data acquiring section 43 receives data from an external device connected via the communication network N in a wired or wireless manner. In the present embodiment, the data acquiring section 43 includes a network interface and the like. The data acquiring section 43 can also be configured by a port or the like into which a USB memory, an SD card, or the like can be inserted.

In the present embodiment, the data acquiring section 43 acquires examination list information from the image server 5, for example. The data acquiring section 43 acquires from the image server 5, the image data of the medical image of the examination specified on the examination list by an operation of the first user (primary radiologist) and the first information described above. Furthermore, the data acquiring section 43 acquires from the image server 5, for example, the image data of the medical image of the examination specified from the examination list by an operation of the second user (secondary radiologist), the first information, and the second information indicating the lesion candidate region detected (specified) by the first user. The image data, the first information, and the second information acquired by the data acquiring section 43 are sent to the controller 41.

Here, the lesion candidate region detected on the medical image by the first user is referred to as a second lesion candidate region. Information indicating the second lesion candidate region (information about the second lesion candidate region) is referred to as second information. The second information is generated for each medical image of a detection source. There may be one second lesion candidate region, there may be a plurality of second lesion candidate regions, or there may be no second lesion candidate region. The second information includes, for example, the kind of lesion, position information, and display information indicating the second lesion candidate region on the medical image for each of the second lesion candidate regions. Display information indicating the second lesion candidate region on the medical image is referred to as second display information. The position information shows coordinates or the like on the medical image. Examples of kinds of lesions include, but not limited to, nodule and mass. The kinds of lesion may be, for example, a lesion that is classified in more detail, such as a nodule type (Solid, P-Solid, GGN, or the like). The second display information is, for example, an annotation. The second display information is different for each kind (or type) of lesion. The annotation as the second display information that is, the annotation indicating the second lesion candidate region is referred to as second annotation information.

In the present embodiment, a case where the second display information is the second annotation information will be described as an example.

A lesion candidate region detected on a medical image by the second user is referred to as a third lesion candidate region. Information indicating the third disease candidate region (information about the third disease candidate region) is referred to as third information. The third information is generated for each medical image of a detection source. There may be one third lesion candidate region, there may be a plurality of third lesion candidate regions, or there may be no third lesion candidate region. The third information includes, for example, the kind of lesion, position information, and display information indicating the third lesion candidate region on the medical image for each of the third lesion candidate regions. Display information indicating the third lesion candidate region on the medical image is referred to as third display information. The position information shows coordinates or the like on the medical image. Examples of the kind of lesion include a nodule and a tumor, and a lesion may be classified into more detailed types such as a nodule type (solid, P-solid, GGN, or the like). The third display information is, for example, an annotation. The third display information is different for each kind (or type) of lesion. The annotation as the third display information, that is, the annotation indicating the third lesion candidate region is referred to as third annotation information.

In the present embodiment, a case where the third display information is the third annotation information will be described as an example.

The data output section 44 includes, for example, a network interface. The data output section 44 outputs data to an external device connected via the communication network N in a wired or wireless manner. In the present embodiment, the data output section 44 includes a network interface and the like. The data output section 44 may be a connector for connecting to an external device, a port of various media such as a USB memory, or the like.

In the present embodiment, the data output section 44 outputs, to the image server 5, the second information indicating the second lesion candidate region specified by the first user (primary radiologist) in the image interpretation terminal 4 and the primary image interpretation finding in association with the identification information of the medical image. Third information indicating a third lesion candidate region specified by the second user (secondary radiologist) and a secondary image interpretation finding created by the second user on the basis of the confirmation result of the first information and the second information are output to the image server 5 in association with the identification information of the medical image.

The operation part 45 includes a keyboard including various keys, a pointing device such as a mouse, or a touch panel attached to the display part 46. The operation part 45 allows a user to perform an input operation. Specifically, the operation part 45 outputs, to the controller 41, an operation signal input by a key operation on the keyboard, a mouse operation, or a touch operation on the touch panel. The operation part 45 functions as a selection means.

The display part 46 includes a monitor such as a liquid crystal display (LCD). The display part 46 displays various screens according to an instruction of a display signal input from the controller 41. Note that the number of monitors is not limited to one, and a plurality of monitors may be provided.

The image server 5 is, for example, a PACS server. The image server 5 associates the medical image output from the modality 1 via the console 2 with patient information, examination information, identification information of the medical image, first information, second information, third information, primary image interpretation finding, secondary image interpretation finding, image interpretation status information of the examination, and the like, and stores them in a database. The image interpretation status information is "not interpreted", "primary image interpretation in progress", "waiting for secondary image interpretation", "secondary image interpretation in progress", "image interpretation completed", or the like.

For example, upon receiving the medical image from the modality 1, the image server 5 stores the medical image in a database in association with patient information, examination information, identification information of the medical image, and image interpretation status information (not interpreted) that are supplementary information of the medical image. Further, when receiving the first information and the identification information of the medical image from the analysis device 3, the image server 5 stores the received first information in the database in association with the medical image and the examination information.

In addition, the image server 5 extracts a record of an examination matching a predetermined condition from the database at predetermined time intervals, generates examination list information including image interpretation status information, and transmits the examination list information to the image interpretation terminal 4. Examples of the predetermined condition include a condition that the examination date and time are within a predetermined period or a condition that the image interpretation status information indicates that image interpretation has not been completed.

In addition, the image server 5 reads the medical image of the examination requested from the image interpretation terminal 4 from the database, transmits the medical image to the image interpretation terminal 4, and updates the image interpretation status information of the examination to, for example, primary image interpretation in progress or secondary image interpretation in progress.

When the image server 5 receives the second information as the primary image interpretation result, the primary image interpretation finding, and the identification information of the medical image from the image interpretation terminal 4, the image server 5 stores the received second information and primary image interpretation finding in the database in association with the medical image and the examination information, and updates the interpretation status information of the examination corresponding to the medical image to "waiting for secondary image interpretation".

Furthermore, when the image server 5 receives the third information as the secondary image interpretation result, the secondary image interpretation finding, and the identification information of the medical image from the image interpretation terminal 4, the image server 5 stores the received third information and secondary image interpretation finding in the database in association with the medical image and the examination information, and updates the image interpretation status information on the examination corresponding to the medical image to "image interpretation completed".

In the medical information display system of the present embodiment, at the time of image interpretation of medical information (medical image), analysis by computer processing (AI analysis) in the analysis device 3 and interpretation by a primary radiologist who is a first user are performed. In the medical information display system, based on the first information and the second information which are the detection results of the lesion candidate region by the computer processing and the first user, respectively, confirmation is performed by the secondary radiologist who is the second user, and a final image interpretation finding (secondary image interpretation finding) is acquired. The image interpretation status information managed by the image server 5 is in accordance with this workflow. The image interpretation terminal 4 displays the examination list information including the image interpretation status information. Thus, each user can recognize the examination to be interpreted. For example, an examination of which the image interpretation status information is "not interpreted" is an examination to be interpreted by the primary radiologist. The examination of which the image interpretation status information is "waiting for secondary image interpretation" is an examination to be interpreted by the secondary radiologist.

The detection result of the first lesion candidate region by the analysis by the computer processing (AI analysis) in the analysis device 3 is also referred to as an analysis result. The detection result of the second lesion candidate region or the third lesion candidate region by the radiologist is also referred to as an image interpretation result.

[Operation of Image Interpretation Terminal]

Next, an operation in a case where the radiologist who is the user interprets the image with the image interpretation terminal 4 will be described.

(Interpretation by a Primary Radiologist)

First, an operation in a case where the primary radiologist interprets will be described.

In the image interpretation terminal 4, the primary radiologist causes the display part 46 to display the examination list information by the operation of the operation part 45 and selects the "uninterpreted" examination from the examination list information by the operation of the operation part 45.

When the examination of "uninterpreted" is selected from the examination list information by the operation of the operation part 45, the controller 41 executes the image interpretation support processing A shown in FIG. 3. The image interpretation support processing A is executed by the controller 41 in cooperation with a program stored in the program storage section 421.

In the image interpretation support processing A, first, the controller 41 causes the data acquiring section 43 to acquire a medical image and first information of a selected examination from the image server 5 (step S1).

For example, the controller 41 transmits the examination ID of the selected examination to the image server 5 via the data output section 44, and requests transmission of the image data of the medical image corresponding to the examination ID and the first information. Thus, the controller 41 causes the data acquiring section 43 to acquire the image data and the first information of the medical image of the selected examination from the image server 5.

Next, the controller 41 causes the display part 46 to display the image interpretation screen 461 on which the acquired medical image is displayed (step S2).

Figure 4:
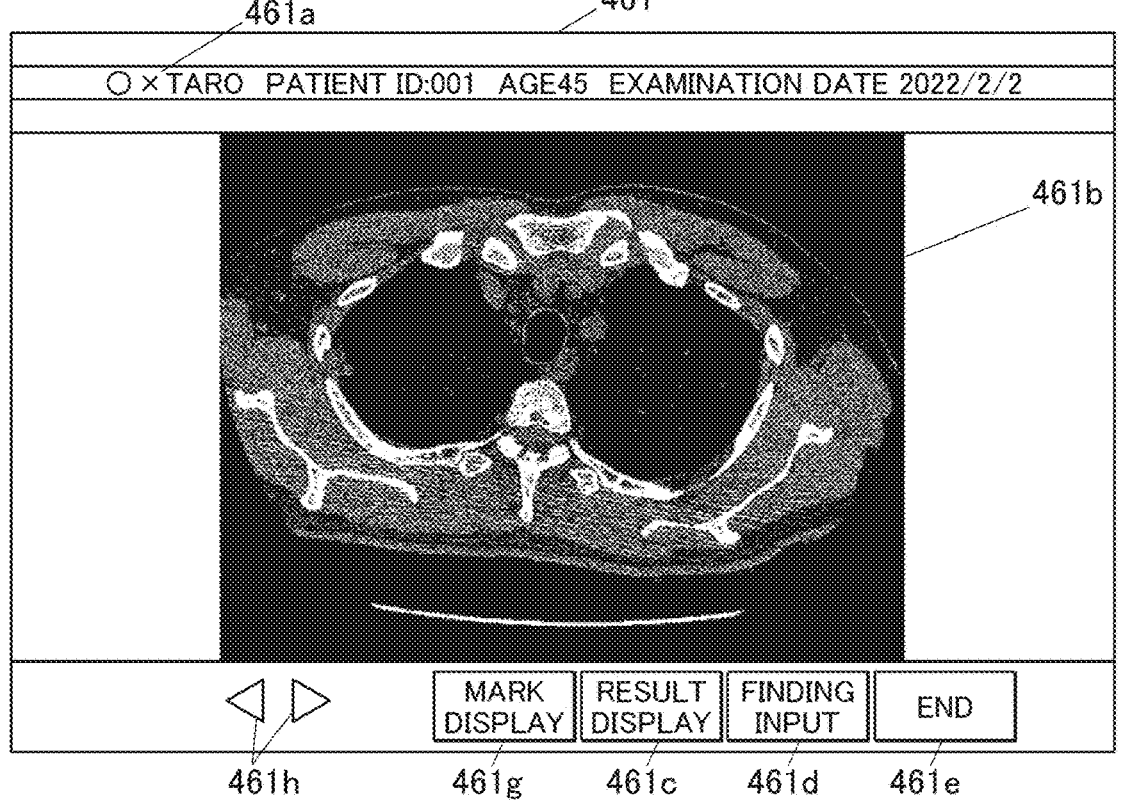
FIG. 4 is a view illustrating an example of an image interpretation screen.

FIG. 4 is a view illustrating an example of the image interpretation screen 461. As shown in FIG. 4, the image interpretation screen 461 is provided with a patient information display field 461a, an image display field 461b, a result display button 461c, a finding input button 461d, an end button 461e, a mark display button 461g, an image switching button 461h, and the like.

The patient information display field 461a displays the patient information.

The image display field 461b displays a medical image.

The result display button 461c is a button for giving an instruction to display the analysis result and the image interpretation result after the image interpretation.

The finding input button 461d is a button for giving an instruction to input an image interpretation finding.

The end button 461e is a button for giving an instruction to end the image interpretation.

The mark display button 461g is a button for giving an instruction to display the analysis result during the interpretation. The analysis result mentioned here is the first annotation information indicating the first lesion candidate region during the primary image interpretation and is the first annotation information and the second annotation information indicating the second lesion candidate region which is the primary image interpretation result during the secondary image interpretation.

An image switching button 461h is a button for switching the medical image to be displayed in a case where there are a plurality of medical images captured in an examination.

Here, in the present embodiment, in order to prevent the radiologist from performing image interpretation while being dragged by the analysis result, in step S2, the medical image is displayed in the image display field 461b without displaying the first annotation information indicating the analysis result. However, when the user presses the mark display button 461g using the operation part 45, the first annotation information indicating the analysis result by the analysis device 3 is displayed, and the user can interpret the image while checking the first annotation information. The primary radiologist interprets the medical image displayed in the image display field 461b, and when detecting a second lesion candidate region which is considered to be a lesion, designates the region (e.g., the center of the region) by the operation part 45.

The controller 41 determines whether or not the mark display button 461g has been pressed to give an instruction to display the first annotation information (step S3).

When it is determined that the display of the first annotation information is instructed (step S3; YES), the controller 41 displays the first annotation information on the medical image displayed in the image display field 461b on the basis of the first information (step S4) and proceeds to step S5.

In a case where it is determined that the display of the first annotation information is not instructed (step S3; NO), the controller 41 proceeds to step S5.

In step S5, the controller 41 determines whether or not the position of the second lesion candidate region is designated by the operation part 45 (step S5).

Figure 5:
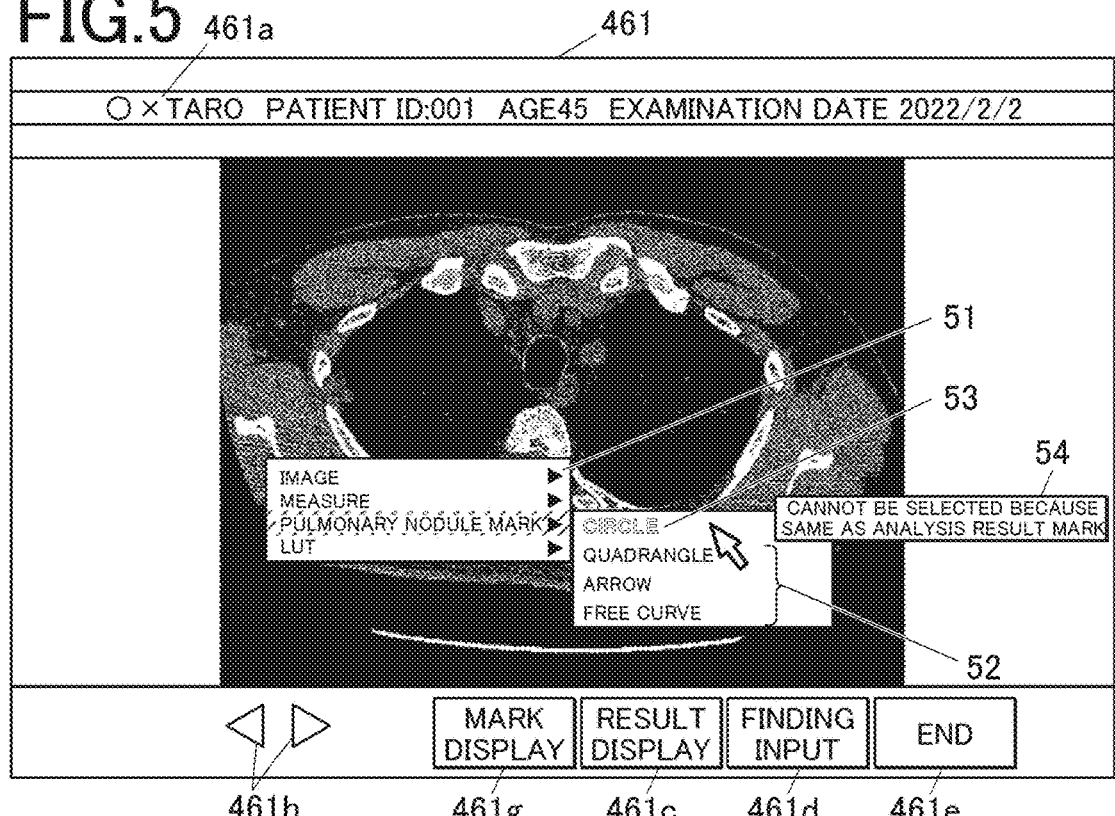
FIG. 5 is a diagram showing an example in which the first display candidate information, the second display candidate information, and the reason why the second display candidate information cannot be selected are displayed on the image interpretation screen.

For example, when the medical image displayed in the image display field 461b is designated (e.g., clicked) by the operation part 45, the controller 41 displays, for example, a menu 51 near the designated position as shown in FIG. 5. The menu 51 is a selection item for the user to select processing to be performed on a specified position. In a case in which an item (e.g., "pulmonary nodule mark") for instructing the addition of a lesion mark is selected from the menu 51, the controller 41 determines that the position of the second lesion candidate region is designated. Note that although not illustrated in FIG. 5, the menu 51 also displays a menu for selecting display of marks of other lesion kinds, such as a "tumor mark", for example, in addition to the "pulmonary nodule mark". Further, without being limited to the display of FIG. 5, addition of a mark for each type (e.g., nodule type such as Solid, P-Solid, and GGN) obtained by further finely classifying the kind of lesion may be selected.

In a case where it is determined that the position of the second lesion candidate region is not designated (step S5; NO), the controller 41 proceeds to step S7.

In a case where it is determined that the position of the second lesion candidate region is designated (step S5; YES), the controller 41 adds the second annotation information to the second lesion candidate region (step S6) and proceeds to step S7.

In Step S6, for example, as illustrated in FIG. 5, the controller 41 displays the first display candidate information 52 corresponding to the second annotation information indicating the candidate region of the selected kind of lesion, that is, serving as a candidate for the second annotation information in the vicinity of the selected item of the menu 51 so as to be selectable. The controller 41 assigns (displays) the annotation information (mark) corresponding to the candidate selected from the first display candidate information 52 to the position of the designated second lesion candidate region as the second annotation information.

Here, in general, the primary radiologist selects the second annotation information from the first display candidate information 52 according to, for example, the operation rule on the medical facility side. However, if the same mark as the first annotation information indicating the analysis result by the analysis device 3 is selected, when the result display button 461c is pressed to finally display the first annotation information indicating the analysis result and the second annotation information indicating the image interpretation result or when the secondary radiologist performs final confirmation, it is not possible to distinguish between the first annotation information indicating the analysis result and the second annotation information indicating the image interpretation result.

In particular, in a case where the next secondary radiologist makes a diagnosis in a state where it is not possible to distinguish between the annotation information by the primary radiologist and the annotation information by the analysis device 3, interpretation needs to be performed in a state where highly reliable annotation information by the user (primary radiologist) and not so reliable annotation information by the analysis device 3, that is, annotation information including many false positives, are mixed. For this reason, there is a possibility that a lesion to be viewed is overlooked. In addition, since the analysis result by the computer cannot be used as the final definitive diagnosis, the radiologist who performs the final definitive diagnosis (the secondary radiologist in the present embodiment) needs to confirm the analysis result of the analysis device 3. In this case, there is a possibility that an analysis result that should actually be viewed is overlooked, and the final diagnosis is determined without confirmation by the secondary radiologist.

Therefore, the controller 41 refers to the first information acquired from the analysis device 3 and performs control so that the same annotation information as the first annotation information indicating the analysis result, that is, the annotation information that cannot be discriminated from the first annotation information is not displayed as the second annotation information indicating the image interpretation result. For example, the controller 41 performs any one of the following (1) to (2).

(1) For example, when displaying the first display candidate information 52, the controller 41 displays information corresponding to second annotation information that can be distinguished from the first annotation information as the first display candidate information 52. At this time, as shown in FIG. 5, the controller 41 displays, together with the first display candidate information 52, the second display candidate information 53 corresponding to the second annotation information that is the same as the first annotation information as display candidate information that cannot be selected. For example, the controller 41 displays the second display candidate information 53 as non-selectable display candidate information by graying out, not allowing pressing, or the like. Furthermore, at that time, the controller 41 preferably notifies the user of the reason why the annotation information corresponding to the second display candidate information 53 is not displayable. For example, as indicated by reference numeral 54 in FIG. 5, the controller 41 may notify the user by displaying the reason why the annotation information corresponding to the second display candidate information 53 cannot be displayed. Alternatively, in a case where the image interpretation terminal 4 comprises a sound output unit, the controller 41 may notify of the reason why the annotation information corresponding to the second display candidate information 53 cannot be displayed by sound.

(2) Alternatively, the controller 41 may display second display candidate information 53 corresponding to second annotation information that is the same as the first annotation information as selectable display candidate information similarly as the first display candidate information 52, together with the first display candidate information 52, as illustrated in the 6A of the drawing. When the second display candidate information 53 is selected by the operation part 45, as illustrated in FIG. 6B, the controller 41 may notify the user of a reason why the second annotation information corresponding to the selected second display candidate information 53 is not displayed and prompt the user to select one from the first display candidate information 52. For example, the controller 41 may pop-up display the notification screen 55 as illustrated in FIG. 6B. Alternatively, in a case where the image interpretation terminal 4 comprises a sound output unit, the controller 41 may perform the notification by sound. Alternatively, as illustrated in FIG. 6C, the controller 41 may display, together with the notification, a message prompting the user to permit changing the second annotation information to annotation information corresponding to one of the first display candidate information 52 rather than the annotation information selected by the user, and a "permit" button 56. The "permit" button 56 is a button for the user to press when permitting to change to annotation information corresponding to one of the first display candidate information 52. Next, when a "permit" button 56 is pressed by the operation part 45 and permission information indicating that the change is permitted can be acquired, the controller 41 may automatically change the second annotation information to annotation information that is different from the selected annotation information and that can be distinguished from the first annotation information and display it. Alternatively, the controller 41 may display the first display candidate information 52 and cause the user to select another candidate, thereby changing the second annotation information to be displayed to annotation information that can be discriminated from the first annotation information and displaying the changed annotation information.

Note that when the first annotation information and the second annotation information are different from each other in at least one of a shape, a line type, a thickness, a color, a brightness, a transparency, and a symbol, the controller 41 determines that the first annotation information and the second annotation information can be distinguished from each other. Alternatively, even when the first annotation information and the second annotation information have the same shape, line type, thickness, color, brightness, transparency, and symbol, the controller 41 may determine that the first annotation information and the second annotation information can be distinguished from each other when at least one piece of identification information of a character or a symbol is added to the second annotation information. That is, the controller 41 displays, as the first display candidate information 52, annotation information which is different from the first annotation information in at least one of shape, line type, thickness, color, brightness, transparency, and symbol, or which is the same as the first annotation information in shape, line type, thickness, color, brightness, transparency, and symbol, and to which identification information of at least one of character or symbol is added. As a result, when the first annotation information as the analysis result and the second annotation information as the image interpretation result are simultaneously displayed, they can be displayed so as to be discriminated from each other.

The controller 41 temporarily stores the position (coordinates) of the second lesion candidate region designated by the operation part 45, the kind of lesion, the second annotation information, and the date and time when the second lesion candidate region is designated or the date and time when the second annotation information is selected in the RAM. In a case where there is a change in the second annotation information, for example, in a case where the user selects the second display candidate information 53 as the second annotation information and then changes the second display candidate information 53 to another piece of first display candidate information 52, the controller 41 temporarily stores the second annotation information before the change and after the change and the date and time that the information was changed in the RAM.

When the input of the image interpretation result, that is, the designation of the second lesion candidate region and the selection of the second annotation information are completed, the primary radiologist presses the result display button 461c to distinguishably display the first annotation information and the second annotation information on the medical image displayed in the image display field 461b, and confirms the analysis result and the image interpretation result. Alternatively, the primary radiologist presses the finding input button 461d to input an image interpretation finding.

In step S7, the controller 41 determines whether or not a result display button 461c has been pressed (step S7).

When determining that the result display button 461c has not been pressed (step S7; NO), the controller 41 proceeds to step S9.

When it is determined that the result display button 461c is pressed (step S7; YES), the controller 41 displays the first annotation information and the second annotation information on the medical image displayed in the image display field 461b at the same time so that the first annotation information and the second annotation information can be discriminated (step S8), and the process proceeds to step S9.

Figure 7:
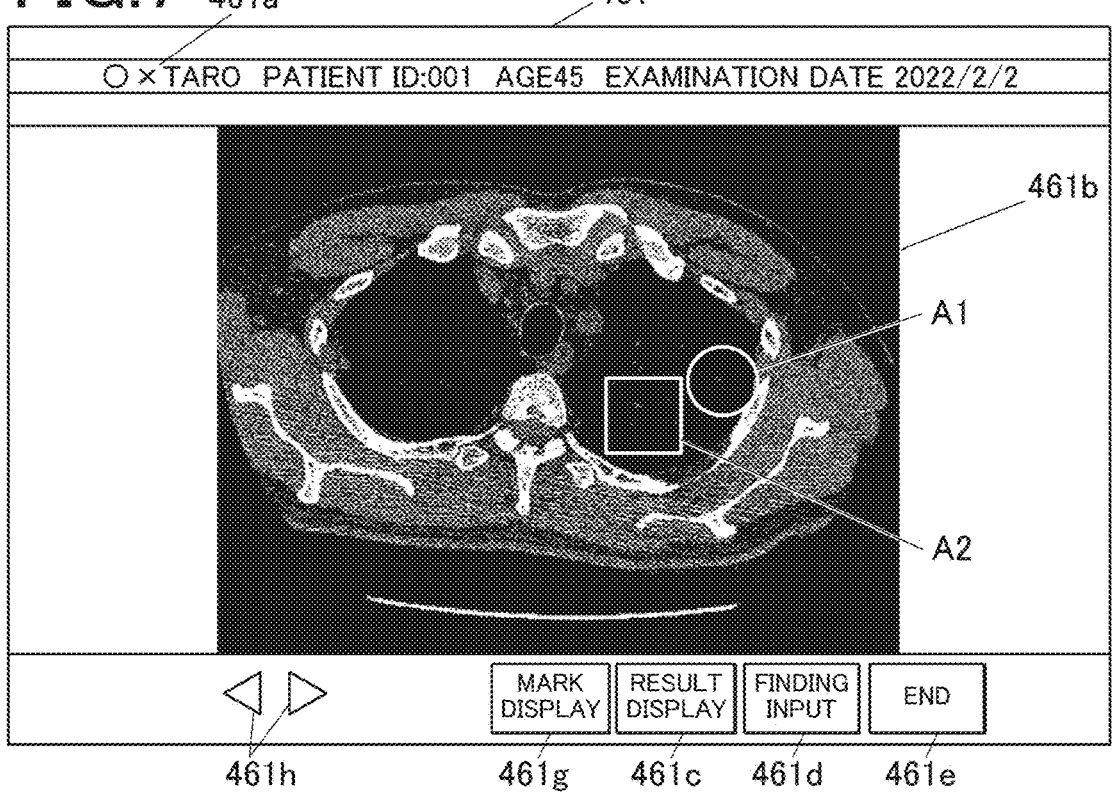
FIG. 7 is a view showing a display example of the image interpretation screen in step S8 of FIG. 3.

FIG. 7 is a view illustrating a display example of an image interpretation screen 461 in step S8. As illustrated in FIG. 7, in step S8, first annotation information A1 indicating the analysis result and second annotation information A2 indicating the image interpretation result are simultaneously displayed on the medical image displayed in the image display field 461b. Since the first annotation information A1 and the second annotation information A2 are different from each other, the first annotation information A1 and the second annotation information A2 are displayed in a distinguishable manner. Therefore, the radiologist can distinguish between the analysis result and the image interpretation result and check each of the results.

In step S9, the controller 41 determines whether or not a finding input button 461d has been pressed (step S9).

When determining that the finding input button 461d has not been pressed (step S9; NO), the controller 41 proceeds to step S11.

Figure 8:
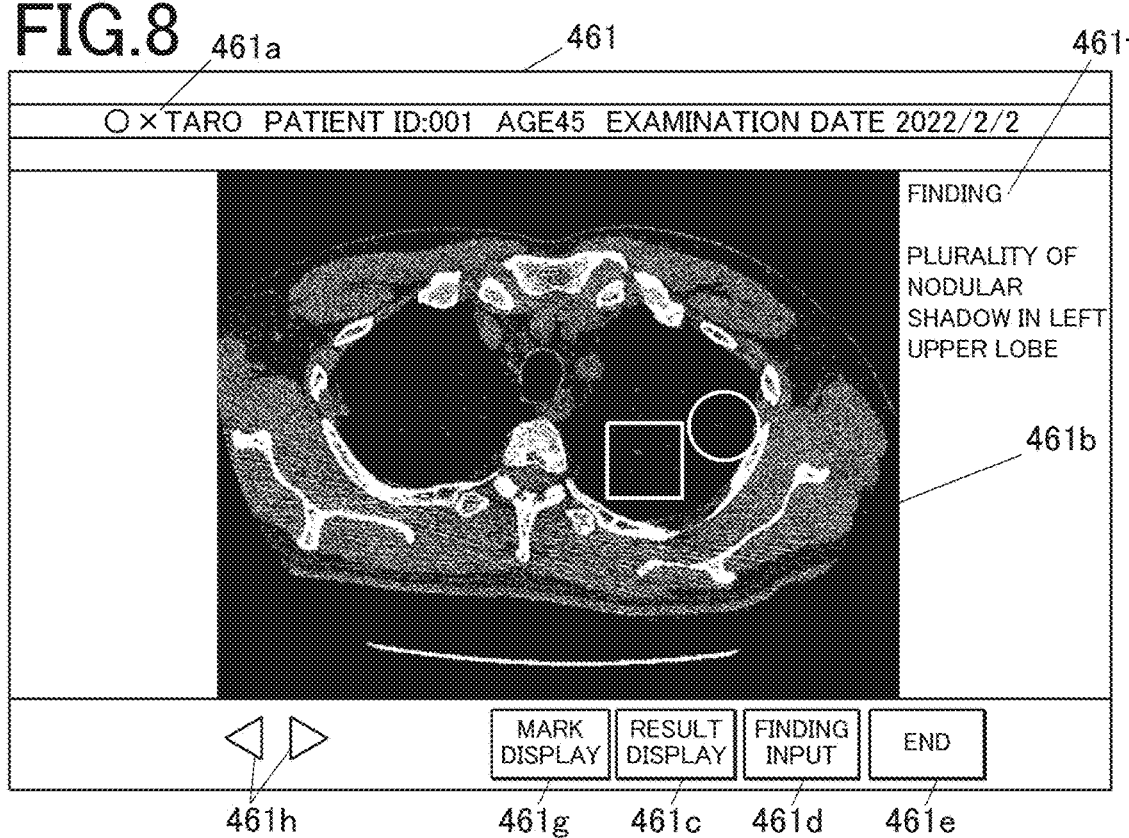
FIG. 8 is a view illustrating an example of an image interpretation finding screen on which an image interpretation finding input field is displayed.

When it is determined that the finding input button 461d is pressed (step S9; YES), the controller 41 displays the image interpretation finding input field 461f on the image interpretation screen 461 as shown in FIG. 8, receives the input of the image interpretation finding (primary image interpretation finding) by the user (primary radiologist) to acquire the primary image interpretation finding (step S10), and proceeds to step S11.

In step S11, the controller 41 determines whether or not the end button 461e is pressed (step S11).

In a case where it is determined that the end button 461e is not pressed (step S11; NO), the controller 41 returns to step S3 and repeatedly executes the processes of steps S3 to S11.

If it is determined that the end button 461e has been pressed (step S11; YES), the controller 41 creates second information indicating the second lesion candidate region (step S12).

In step S12, based on the information temporarily stored in the RAM, the controller 41 creates second information including the position (coordinates) of the second lesion candidate region, the kind of lesion, and the second annotation information designated by the operation part 45 until it is determined in step S11 that the end button 461e has been pressed in a file of a predetermined format. Identification information of the medical image corresponding to the second information and a time stamp at a time point when the second information is input are assigned to the file of the second information. If the second annotation information is changed before it is determined in step S11 that the end button 461e is pressed, the controller 41 creates files of the second information before and after the change. In addition, in a case where the second lesion candidate region is not detected, for example, information indicating this is created as the second information. The case where the second annotation information is changed is, for example, a case where the user selects the second display candidate information 53 as the second annotation information and then changes the second annotation information to another piece of first display candidate information 52.

The controller 41 stores the created second information and primary image interpretation findings in the storage section 42 in association with the medical image (identification information on the medical image, patient information, and examination information) (step S13). The controller 41 outputs the second information and the primary image interpretation findings to the image server 5 in association with the identification information of the medical image through the data output section 44 (step S14), and ends the image interpretation support processing A. In a case where the second annotation information is changed, the second information in the description of step S13 and the S14 refers to the second information before and after the change.

Upon receiving the second information and the primary image interpretation finding from the image interpretation terminal 4, the image server 5 stores the received second information and primary image interpretation finding in a database in association with the medical image and the examination information. Then, the image server 5 updates the image interpretation status information of the examination corresponding to the received medical image to "waiting for secondary image interpretation".

(Image Interpretation by Secondary Radiologist)

Next, a description will be given of operations performed when the secondary radiologist performs image interpretation.

The secondary radiologist displays the examination list information on the display part 46 by operating the operation part 45 in the image interpretation terminal 4 and selects the examination with "waiting for secondary image interpretation" from the examination list information by operating the operation part 45.

Figure 9:
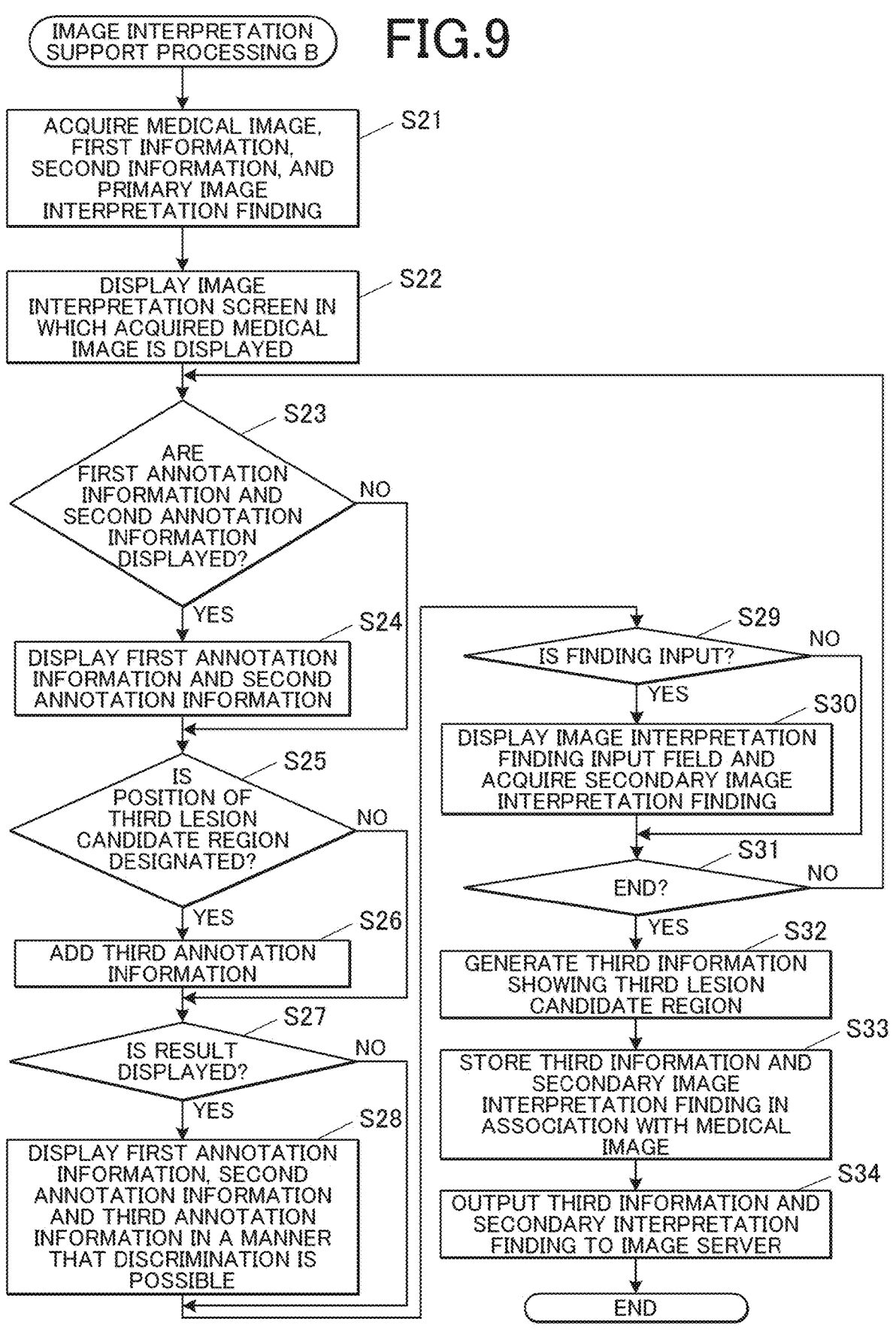
FIG. 9 is a flowchart showing the flow of image interpretation support processing B executed by the controller in FIG. 2.

When the examination of "waiting for secondary image interpretation" is selected from the examination list information by the operation of the operation part 45, the controller 41 executes the image interpretation support processing B shown in FIG. 9. The image interpretation support processing B is executed by the controller 41 in cooperation with a program stored in the program storage section 421.

In the image interpretation support processing B, first, the controller 41 causes the data acquiring section 43 to acquire the medical image, the first information, the second information, and the primary image interpretation finding of the selected examination from the image server 5 (step S21).

For example, the controller 41 transmits the examination ID of the selected examination to the image server 5 through the data output section 44, and requests transmission of the image data of the medical image corresponding to the examination ID, the first information, the second information, and the primary image interpretation finding. Accordingly, the controller 41 acquires the medical image data, the first information, the second information, and the primary image interpretation finding of the selected examination from the image server 5 by the data acquiring section 43.

Next, the controller 41 causes the display part 46 to display the image interpretation screen 461 on which the acquired medical image is displayed (step S22).

The image interpretation screen 461 displayed in step S22 is the same as that illustrated in FIG. 4.

The secondary radiologist interprets the displayed medical image on the image interpretation screen 461. When a third lesion candidate region which is considered to be a lesion is detected, the secondary radiologist designates the region (e.g., the center of the region) by the operation part 45. Furthermore, the secondary radiologist can press a mark display button 461g to cause the first annotation information and the second annotation information to be displayed on the medical image and perform interpretation based on the confirmation results.

The controller 41 determines whether or not the mark display button 461g is pressed to instruct to display the first annotation information and the second annotation information (step S23).

When it is determined that the instruction to display the first annotation information and the second annotation information is given (step S23; YES), the controller 41 displays the first annotation information and the second annotation information at the same time on the medical image displayed in the image display field 461b based on the first information and the second information so that the first annotation information and the second annotation information can be discriminated (step S24), and the process proceeds to step S25.

As described above, in the image interpretation support processing A, the second annotation information different from the first annotation information is assigned. Therefore, the first annotation information and the second annotation information are displayed so as to be distinguishable from each other. Therefore, the secondary radiologist can distinguish the analysis result from the image interpretation result of the primary radiologist, and it is possible to prevent a lesion to be seen from being overlooked.

In a case where it is determined that the display of the first annotation information and the second annotation information is not instructed (step S23; NO), the controller 41 proceeds to step S25.

In step S25, the controller 41 determines whether or not the position of a third lesion candidate region has been specified by the operation part 45 (step S25).

For example, when the medical image displayed in the image display field 461b is designated (clicked) by the operation part 45, the controller 41 displays, for example, a menu 51 for selecting processing to be performed on the designated position near the designated position, as shown in FIG. 5. In a case in which an item (e.g., "pulmonary nodule mark") for instructing the addition of a lesion mark is selected from the menu 51, the controller 41 determines that the position of the third lesion candidate region is designated. Note that although not illustrated in FIG. 5, the menu 51 also displays a menu for selecting display of marks of other lesion kinds, such as a "tumor mark", in addition to the "pulmonary nodule mark". Furthermore, the menu 51 is not limited to the display of FIG. 5 and may be displayed such that the addition of a mark for each type (e.g., a nodule type such as Solid, P-Solid, or GGN) obtained by further finely classifying the kind of lesion can be selected.

In a case where it is determined that the position of the third lesion candidate region is not designated (step S25; NO), the controller 41 proceeds to step S27.

In a case where it is determined that the position of the third lesion candidate region is designated (step S25; YES), the controller 41 adds the third annotation information indicating the third lesion candidate region to the third lesion candidate region (step S26) and proceeds to step S27.

Here, the controller 41 assigns information different from the first annotation information as the third annotation information indicating the third disease candidate region detected by the secondary radiologist. On the other hand, the third annotation information may be the same as or different from the second annotation information. Whether or not the third annotation information is set to be the same as the second annotation information can be set in advance by the user by operating the operation part 45, for example.

For example, in a case where the third annotation information is set to be the same as the second annotation information, for example, when the addition of the mark of the kind of lesion included in the second information is selected from the menu 51 of FIG. 5, the controller 41 automatically selects the same annotation information as the second annotation information corresponding to the selected kind of lesion as the third annotation information, and displays the same annotation information in the third lesion candidate region designated by the user. Thus, when the analysis result and the image interpretation result of the radiologist are displayed at the same time, the analysis result and the image interpretation result of the radiologist can be displayed in a distinguishable manner.

In addition, for example, in a case where the third annotation information is set to be different from the second annotation information, the controller 41 causes the user to select the display candidate information corresponding to the third annotation information and displays the third annotation information, for example, by any one of the methods (1) and (2) described in Step S6 of the above-described image interpretation support processing A. At this time, the controller 41 displays the third display candidate information, which is a candidate for the third annotation information, instead of displaying the first display candidate information 52, which is a candidate for the second annotation information. The third display candidate information is annotation information that is not used as any of the first annotation information and the second annotation information. Further, the controller 41 displays the fourth display candidate information corresponding to the same annotation as the first annotation information or the second annotation information instead of the display of the second display candidate information 53. The controller 41 performs control so that the user selects information corresponding to the third annotation information from among the third display candidate information rather than the fourth display candidate information.

Accordingly, when the first annotation information which is the analysis result, the second annotation information which is the image interpretation result of the primary radiologist, and the third annotation information which is the image interpretation result of the secondary radiologist are displayed at the same time, they can be displayed so as to be discriminated from each other.

The controller 41 temporarily stores, in the RAM, the position (coordinates) of the third lesion candidate region designated by the operation part 45, the kind of lesion, the third annotation information, and the date and time when the third lesion candidate region is designated or the date and time when the third annotation information is selected. When the third annotation information is changed, for example, when the user selects the fourth display candidate information as the third annotation information and then changes the fourth display candidate information to another third display candidate information, the controller 41 temporarily stores the third annotation information before and after the change and the date and time of the change in the RAM.

When the input of the image interpretation result, that is, the input of the third annotation information is completed, the secondary radiologist presses the result display button 461c to display the first annotation information, the second annotation information, and the third annotation information on the medical image displayed in the image display field 461b and confirms the analysis result and the image interpretation result. Alternatively, the secondary radiologist presses the finding input button 461d to input an image interpretation finding (secondary image interpretation finding).

In step S27, the controller 41 determines whether or not a result display button 461c has been pressed (step S27).

When determining that the result display button 461c has not been pressed (step S27; NO), the controller 41 proceeds to step S29.

If the controller 41 determines that the result display button 461c has been pressed (YES in step S27), the controller 41 displays the first annotation information, the second annotation information, and the third annotation information on the medical image displayed in the image display field 461b at the same time in a distinguishable manner (step S28) and shifts to step S29.

Here, when an annotation different from the second annotation information is added as the third annotation information in step S26, the first annotation information indicating the analysis result by the analysis device 3, the second annotation information indicating the image interpretation result by the primary radiologist, and the third annotation information indicating the image interpretation result by the secondary radiologist are distinguishably displayed in step S28. Therefore, the secondary radiologist can confirm the first annotation information and the second annotation information, make a definite diagnosis based on the confirmation result and his/her image interpretation result, and create an image interpretation finding.

If the same annotation as the second annotation information is added as the third annotation information in step S26, the analysis result and the image interpretation result by the radiologist are distinguishably displayed in step S28. Therefore, the secondary radiologist can create an image interpretation finding by distinguishing and confirming the analysis result of the computer and the image interpretation result by the radiologist.

In any case, since the analysis result by the analysis device 3 and the image interpretation result of the radiologist are displayed in distinction from each other, it is possible to prevent the user from overlooking a highly reliable image interpretation result such as a lesion candidate region detected by the primary radiologist or performing a definitive diagnosis without confirming an analysis result by computer processing which should be originally viewed.

Note that the image interpretation screen 461 may be provided with switching buttons for instructing switching of ON/OFF of display of each annotation information, for example, a first switching button, a second switching button, and a third switching button, so that the user can switch the annotation to be displayed on the medical image. The first switching button is a button for switching ON/OFF of the first annotation information. The second switching button is a button for switching ON/OFF of the second annotation information. The third switching button is a button for switching ON/OFF of the third annotation information. For example, a configuration may be adopted in which each piece of annotation information can be displayed on a medical image, or the display thereof can be deleted by operating these switching buttons. Thus, the secondary radiologist can efficiently interpret the image.

In step S29, the controller 41 determines whether or not a finding input button 461d has been pressed (step S29).

In a case in which it is determined that the finding input button 461d is not pressed (Step S29; NO), the controller 41 proceeds to Step S31.

When determining that the finding input button 461d has been pressed (step S29; YES), as illustrated in FIG. 8, the controller 41 displays an image interpretation finding input field 461f on the image interpretation screen 461, accepts an input of an image interpretation finding by a secondary radiologist who is a second user, and acquires a secondary image interpretation finding (step S30), and proceeds to step S31.

The secondary image interpretation findings may be created as findings different from the primary image interpretation findings or may be created by the secondary radiologist correcting the primary image interpretation findings. The secondary radiologist makes a definitive diagnosis based on the analysis result, the primary image interpretation result, and the secondary image interpretation result, and creates a secondary image interpretation finding.

In step S31, the controller 41 determines whether or not the end button 461e is pressed (step S31).

In a case where it is determined that the end button 461e is not pressed (step S31; NO), the controller 41 returns to step S23 and repeatedly executes the processes of steps S23 to S31.

When it is determined that the end button 461e has been pressed (step S31; YES), the controller 41 creates third information indicating a third lesion candidate region (step S32).

In Step S32, the controller 41 creates third information including the position (coordinates) of the third lesion candidate region, the kind of lesion, and the third annotation information designated by the operation part 45 until it is determined that the end button 461e has been pressed in Step S31, in a predetermined format file, on the basis of the information temporarily stored in the RAM. Identification information of the medical image corresponding to the third information and a time stamp at a time point when the third information is input are assigned to the file of the third information. When the third annotation information is changed before it is determined in step S31 that the end button 461e is pressed, for example, when the user selects the fourth display candidate information that cannot be used as the third annotation information and then changes the fourth display candidate information to another third display candidate information, the controller 41 creates files of the third information before and after the change. In addition, in a case in which the third lesion candidate region is not detected, the controller 41 creates, for example, information indicating that effect as the third information.

Then, the controller 41 stores the created third information and secondary image interpretation findings in the storage section 42 in association with the medical image (identification information of the medical image, patient information, and examination information) (step S33). The controller 41 outputs the third information and the secondary image interpretation findings to the image server 5 in association with the identification information of the medical image through the data output section 44 (step S34), and the image interpretation support processing B ends. The third information in the description of steps S33 and S34 refers to the third information before and after the change when the third annotation information is changed.

In a case where the image server 5 receives the third information and the secondary image interpretation findings from the image interpretation terminal 4, the image server 5 stores the received third information and secondary image interpretation findings in association with the medical image and the examination information in the database. Then, the image interpretation status information of the examination corresponding to the received medical image is updated to the interpretation completion.

Second Embodiment

In the first embodiment, the controller 41 performs control such that annotation information different from the first annotation information is selected when the user selects the second annotation information in order to display the first annotation information and the second annotation information in a distinguishable manner. However, the second annotation information that can be discriminated from the first annotation information may be stored in the storage section 42 in advance, and the controller 41 may display the second annotation information with reference to the second annotation information stored in the storage section 42.

For example, after the first information is generated by the AI analysis, the analysis device 3 refers to the first information, allocates in advance the annotation information that is not used as the first annotation information and can be discriminated from the first annotation information as the second annotation information of the kind (or type) of each lesion, and transmits the allocation information to the image server 5 together with the first information and the identification information of the medical image of the detection source.

The image server 5 stores the received first information and assignment information in a database in association with the medical image and the examination information.

When acquiring the medical image of the selected examination and the first information, the data acquiring section 43 of the image interpretation terminal 4 also acquires the allocation information. The controller 41 stores the acquired allocation information in the storage section 42. When displaying the second annotation information in the designated second lesion candidate region, the controller 41 displays the second annotation information with reference to the allocation information stored in the storage section 42.

Accordingly, when the controller 41 simultaneously displays the first annotation information and the second annotation information on the display part 46, the controller 41 can distinguishably display the first annotation information and the second annotation information.

The allocation information of the second annotation information is not limited to being generated by the analysis device 3 and may be generated by the image server 5 or the image interpretation terminal 4, for example.

As described above, when first display information (e.g., first annotation information) indicating a first lesion candidate region obtained by computer processing of medical information and second display information (e.g., second annotation information) indicating a second lesion candidate region specified by a user based on the medical information are simultaneously displayed on the display part 46, the controller 41 of the image interpretation terminal 4 displays the first display information and the second display information in a distinguishable manner.

Therefore, when the detection result of the first lesion candidate region by the computer processing on the medical information and the detection result of the second lesion candidate region by the user are displayed and interpreted by a doctor, it is possible to distinguish whether the display information displayed on the medical image is the first display information indicating the detection result by the analysis device 3 or the second display information indicating the detection result by the user. As a result, it is possible to prevent the doctor from overlooking the lesion to be viewed.

For example, when simultaneously displaying the first display information indicating the detection result by the analysis device 3 and the second display information indicating the detection result by the primary radiologist, the controller 41 displays the first display information and the second display information in a distinguishable manner. Therefore, it is possible to support the secondary radiologist to efficiently and accurately create an image interpretation finding based on the detection result of the analysis device 3 and the confirmation result of the detection result by the primary radiologist.

For example, the controller 41 displays the first display candidate information corresponding to the second display information distinguishable from the first display information so as to be selectable and displays the selected first display candidate information as the second display information. Therefore, the second display information which can be discriminated from the first display information can be displayed.

Further, for example, the controller 41 displays the first display candidate information in a selectable manner. On the other hand, the controller 41 displays the second display candidate information corresponding to the second display information which is the same as the first display information as the display candidate information which cannot be selected and notifies the user of the reason why it cannot be selected. Therefore, it is possible to prevent the user from selecting the second information which cannot be discriminated from the first display information, and to display the second display information which can be discriminated from the first display information.

Further, for example, the controller 41 displays the first display candidate information in a selectable manner and displays the second display candidate information corresponding to the same second display information as the first display information as selectable display candidate information. When the second display candidate information is selected, the controller 41 notifies the user of a reason for not displaying the second display information. Therefore, even when the user selects the second information that cannot be discriminated from the first display information, it is possible to prevent the second information from being displayed as the second display information. Therefore, the second display information which can be discriminated from the first display information can be displayed.

In addition, when the user selects the second information that cannot be discriminated from the first display information, the controller 41 acquires permission information indicating that the user permits the second display information to be changed. When the permission information is acquired, the controller 41 changes the second display information. Accordingly, the first display information and the second display information can be displayed in a distinguishable manner.

In addition, for example, when the second display information is changed, the controller 41 stores the second display information before the change corresponding to the changed second display information in the storage section 42. Therefore, it is possible to save a history of the second display information.

Further, for example, the controller 41 displays the first display information and the second display information in a distinguishable manner by differentiating at least one selected from the group consisting of the shape, the line type, the thickness, the color, the brightness, the transparency, and the symbol. Alternatively, the controller 41 adds at least one piece of identification information of a character or a symbol to the second display information to display the second display information in a distinguishable manner. Accordingly, the user can easily distinguish between the first display information and the second display information.

Further, for example, the controller 41 stores second display information that can be discriminated from first display information indicating the first lesion candidate region in the storage section 42 and displays the second display information based on the information stored in the storage section 42. Accordingly, the first display information and the second display information can be displayed so as to be distinguished from each other.

Note that the present invention is not limited to the above-described embodiment, and various modifications can be made without departing from the spirit and scope of the present invention.

For example, in the above embodiment, the case where the medical information of the present invention is a medical image has been described as an example. However, the medical information is not limited to the medical image.

Information acquired by various examinations on a patient and the like may be broadly included in the medical information. For example, results obtained by various examinations or the like such as electrocardiogram waveform data, cardiac sound data, and data related to blood flow may also be included in the medical information. Next, the present invention may be applied to a case where AI analysis is performed on these pieces of medical information and first display information indicating a result of the AI analysis and second display information indicating an image interpretation result of a doctor are displayed in the medical information.

In the above-described embodiment, the first display information is not changed, and the second display information different from the first display information is selected. However, in a case where the second display information is determined in advance by a facility or the like, the first display information may be changed to information capable of discriminating from the second display information without changing the second display information.

While a case where the first information including the first display information is acquired in the GSPS format is illustratively described in the embodiment, the present disclosure is not limited thereto, and the first information may be acquired in a structured report (SR) format. In addition, an image (screen capture image) in which the first display information (first annotation information) is displayed on the medical image may be generated by the analysis device 3 and may be acquired and used as the first display information.

In the above-described embodiment, the case where the user selects the second display information has been described as an example. However, for example, when the second display information is determined in advance according to the kind of lesion (type) in a medical facility or the like, the information may be stored in the storage section 42, and when the kind of lesion and the second lesion candidate region are designated by the operation part 45, the controller 41 may display the second display information based on the information stored in the storage section 42. In a case where the second display information of the designated kind of lesion cannot be distinguished from (is identical to) the first display information of any of the first lesion candidate regions, the controller 41 may display, for example, the user interface illustrated in FIG. 5 or FIG. 6A to FIG. 6C and cause the user to select the second display information that can be distinguished from the first display information. Alternatively, the controller 41 may automatically select the second display information that can be distinguished from the first display information according to a predetermined priority and display the second display information.

In the above-described embodiment, the analysis device 3, the image interpretation terminal 4, and the image server 5 are illustrated as independent apparatuses in FIG. 1. However, the image interpretation terminal 4 and the image server 5, the analysis device 3 and the image server 5, and the analysis device 3, the image interpretation terminal 4, and the image server 5 may be configured as a single apparatus (display apparatus).

The functions executed by the controller 41 of the image interpretation terminal 4 may be distributed to a plurality of hardware processors or hardware processors of a plurality of apparatuses.

Further, in the above description, an example in which a hard disk, a semiconductor nonvolatile memory, or the like is used as a computer-readable medium of the program according to the present invention has been disclosed, but the present invention is not limited to this example. As other computer-readable media, portable recording media such as CD-ROMs can be applied. Furthermore, a carrier wave is also applied as a medium for providing data of the program according to the present invention via a communication line.

In addition, the detailed configuration and detailed operation of each device constituting the medical information display system can be appropriately changed without departing from the scope of the invention.

Although some embodiments of the present invention have been described, the scope of the present invention is not limited to the above-described embodiments and includes the scope of the invention described in the claims and its equivalent scope.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A display apparatus comprising:
a hardware processor configured to cause a display part to simultaneously display first display information indicating a first lesion candidate region obtained by computer processing on medical information and second display information indicating a second lesion candidate region specified by a user on the basis of the medical information,
wherein, in a case where the first display information and the second display information are displayed at the same time, the hardware processor distinguishably displays the first display information and the second display information,
wherein the hardware processor is configured to perform control to selectively display first display candidate information for adding the second display information,
wherein the display apparatus further includes an operation part with which the user selects the first display candidate information, and
wherein the first display candidate information is information corresponding to the second display information that is distinguishable from the first display information.

2. A display apparatus according to claim 1, comprising:
a hardware processor configured to,
acquire first information indicating a first lesion candidate region obtained by computer processing on medical information,
acquire second information indicating a second lesion candidate region specified by a first user based on the medical information,
cause a display part to simultaneously display first display information based on the first information and second display information based on the second information, and
acquire an image interpretation finding created by a second user based on the medical information, wherein, in a case where the first display information and the second display information are displayed at the same time, the hardware processor distinguishably displays the first display information and the second display information, and
wherein the hardware processor acquires the image interpretation finding based on a confirmation result of the first display information and the second display information by the second user.

3. The display apparatus according to claim 1, wherein the hardware processor displays the first display candidate information in a selectable manner and displays second display candidate information corresponding to the second display information identical to the first display information as display candidate information that cannot be selected.

4. The display apparatus according to claim 3, wherein when the hardware processor causes the second display candidate information to be displayed as non-selectable display candidate information, the hardware processor notifies the user of a reason why the second display candidate information is non-selectable.

5. The display apparatus according to claim 1,
wherein the hardware processor displays the first display candidate information in a selectable manner, and displays second display candidate information corresponding to the second display information identical to the first display information as selectable display candidate information, and
wherein in a case where the second display candidate information is selected, a reason for not displaying the second display information is notified to the user.

6. The display apparatus according to claim 5,
wherein the hardware processor obtains permission information that permits the second display information to be changed, and
wherein in a case where the permission information is acquired, the first display information and the second display information are caused to be displayed in a distinguishable manner by changing the second display information.

7. The display apparatus according to claim 6, further comprising a storage section configured to store, when the second display information is changed, the second display information before the change corresponding to the changed second display information.

8. The display apparatus according to claim 1, wherein the hardware processor causes the first display information and the second display information to be distinguishably displayed by differentiating at least one selected from the group consisting of a shape, a line type, a thickness, a color, brightness, transparency, and a symbol between the first display information and the second display information.

9. The display apparatus according to claim 1, wherein the hardware processor adds identification information of at least one of a character and a symbol to the second display information to display the first display information and the second display information in a distinguishable manner.

10. The display apparatus according to claim 1, wherein the first display information is first annotation information, and the second display information is second annotation information.

11. The display apparatus according to claim 1, further comprising a storage section in which the second display information that can be distinguished from the first display information indicating the first lesion candidate region is stored.

12. A medical information display system comprising:
a display apparatus comprising:

a hardware processor configured to cause a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the hardware processor distinguishably displays the first display information and the second display information, wherein the hardware processor is configured to perform control to selectively display first display candidate information for adding the second display information, wherein the display apparatus further includes an operation part with which the user selects the first display candidate information, and wherein the first display candidate information is information corresponding to the second display information that is distinguishable from the first display information.

13. A medical information display system according to claim 12, comprising:

a hardware processor configured to, acquire first information indicating a first lesion candidate region obtained by computer processing on medical information, acquire second information indicating a second lesion candidate region specified by a first user based on the medical information, cause a display part to simultaneously display first display information based on the first information and second display information based on the second information, and acquire an image interpretation finding created by a second user based on the medical information, wherein, in a case where the first display information and the second display information are displayed at the same time, the hardware processor distinguishably displays the first display information and the second display information and acquires the image interpretation finding based on a confirmation result of the first display information and the second display information by the second user.

14. A non-transitory recording medium storing a computer-readable program causing a computer of a display apparatus to perform, causing a display part to simultaneously display first display information indicating a first lesion candidate region obtained by computer processing on medical information and second display information indicating a second lesion candidate region specified by a user on the basis of the medical information, wherein, in a case where the first display information and the second display information are displayed at the same time, the first display information and the second display information are distinguishably displayed, wherein the computer is configured to perform control to selectively display first display candidate information for adding the second display information, wherein the display apparatus further includes an operation part with which the user selects the first display candidate information, and wherein the first display candidate information is information corresponding to the second display information that is distinguishable from the first display information.

15. A non-transitory recording medium according to claim 14 storing a computer-readable program causing a computer to perform, first acquiring to acquire first information indicating a first lesion candidate region obtained by computer processing on medical information, second acquiring to acquire second information indicating a second lesion candidate region specified by a first user based on the medical information, displaying to cause a display part to simultaneously display first display information based on the first information and second display information based on the second information, and third acquiring to acquire an image interpretation finding created by a second user based on the medical information, wherein in a case where the first display information and the second display information are displayed at the same time, in the displaying, the first display information and the second display information are distinguishably displayed, and wherein in the third acquiring, the image interpretation finding is acquired based on a confirmation result of the first display information and the second display information by the second user.

16. A display method comprising:

causing a display part to simultaneously display first display information indicating a first lesion candidate region obtained by computer processing on medical information and second display information indicating a second lesion candidate region specified by a user on the basis of the medical information, and in a case where the first display information and the second display information are displayed at the same time, distinguishably displaying the first display information and the second display information, performing control to selectively display first display candidate information for adding the second display information, selecting, by the user, the first display candidate information, wherein the first display candidate information is information corresponding to the second display information that is distinguishable from the first display information.

17. A display method accordingly to claim 16 comprising:

first acquiring to acquire first information indicating a first lesion candidate region obtained by computer processing on medical information, second acquiring to acquire second information indicating a second lesion candidate region specified by a first user based on the medical information, displaying to cause a display part to simultaneously display first display information based on the first information and second display information based on the second information, and third acquiring to acquire an image interpretation finding created by a second user based on the medical information, wherein, in a case where the first display information and the second display information are displayed at the same time, in the displaying, the first display information and the second display information are distinguishably displayed, and in the third acquiring, the image interpretation finding is acquired based on a confirmation result of the first display information and the second display information by the second user.

\* \* \* \* \*